United States Patent
Winings et al.

(10) Patent No.: US 6,882,278 B2
(45) Date of Patent: Apr. 19, 2005

(54) APPARATUS AND METHODS FOR MONITORING COMPLIANCE WITH RECOMMENDED HAND-WASHING PRACTICES

(75) Inventors: Thomas R. Winings, Providence, UT (US); Layne W. Finlinson, Smithfield, UT (US); M. Wade Miller, Hyrum, UT (US); Clayton R. Carter, North Logan, UT (US)

(73) Assignee: Path-X International, Inc., Logan, UT (US)

( * ) Notice: Subject to any disclaimer, the term of this patent is extended or adjusted under 35 U.S.C. 154(b) by 50 days.

(21) Appl. No.: 10/395,038

(22) Filed: Mar. 21, 2003

(65) Prior Publication Data

US 2004/0001009 A1 Jan. 1, 2004

Related U.S. Application Data

(60) Provisional application No. 60/367,124, filed on Mar. 22, 2002.

(51) Int. Cl.[7] .............................................. G08B 23/00
(52) U.S. Cl. ................................ 340/573.1; 340/573.4; 4/623
(58) Field of Search .................... 340/573.1, 573.4; 4/623, 661

(56) References Cited

U.S. PATENT DOCUMENTS

| 5,202,666 | A | | 4/1993 | Knippscheer |
| 5,945,910 | A | * | 8/1999 | Gorra ...................... 340/573.1 |
| 6,236,317 | B1 | * | 5/2001 | Cohen et al. ............ 340/573.1 |
| 6,392,546 | B1 | | 5/2002 | Smith |
| 6,426,701 | B1 | * | 7/2002 | Levy et al. .............. 340/573.1 |
| 6,727,818 | B1 | * | 4/2004 | Wildman et al. ........ 340/573.1 |
| 2003/0030562 | A1 | * | 2/2003 | Lane et al. .............. 340/573.4 |

* cited by examiner

Primary Examiner—Jeffery Hofsass
Assistant Examiner—Anne V. Lai
(74) Attorney, Agent, or Firm—Madson & Metcalf

(57) ABSTRACT

A method for monitoring compliance with recommended hand-washing practices is disclosed. The method involves detecting the occurrence of an event that is specified in a hand-washing rule. The method also involves determining whether a person who is involved in the event complies with the hand-washing rule. If the person does not comply with the hand-washing rule, the method may involve triggering a reminder alarm. The method may also involve determining whether the person washes his or her hands within a period of time subsequent to the reminder alarm. Compliance data that is related to compliance with the hand-washing rule may be updated.

23 Claims, 5 Drawing Sheets

APPARATUS AND METHODS FOR MONITORING COMPLIANCE WITH RECOMMENDED HAND-WASHING PRACTICES

RELATED APPLICATIONS

This application is related to and claims priority from U.S. patent application Ser. No. 60/367,124 filed Mar. 22, 2002, for "Hand-Washing Compliance Apparatus and Method," with inventors Thomas R. Winings, Layne W. Finlinson, M. Wade Miller, and Clayton R. Carter, which is incorporated herein by reference.

TECHNICAL FIELD

The present invention relates generally to the prevention of disease. More specifically, the present invention relates to apparatus and methods for monitoring compliance with recommended hand-washing practices.

BACKGROUND

Infectious diseases are caused by various types of microscopic germs such as viruses, bacteria, parasites and fungi. These germs cause illnesses that range from the common cold or flu to disabling conditions such as Lyme disease and polio to deadly diseases like hantavirus infection and AIDS. Reducing the spread of infectious diseases is an important issue facing society today.

One of the most effective ways to reduce the spread of infectious diseases involves the seemingly simple task of hand-washing. Indeed, many studies have demonstrated a clear correlation between improved hand hygiene and reduced infection rates. As used herein, the term "hand-washing" may refer to the action of washing hands in water with bland soap (i.e., soap that does not have any type of disinfectant). Hand-washing may also refer to any action where an antimicrobial solution is used to clean and decontaminate the hands.

Concern with avoiding the spread of infectious diseases is particularly high in institutions that deal with the public, such as hospitals and other healthcare facilities, restaurants, libraries, schools, airports, and the like. In order to safeguard employees, patrons, and others from unsanitary conditions, many of these institutions have developed certain recommended hand-washing practices. For example, in the healthcare industry it is generally recommended that healthcare workers wash their hands before entering a patient's room and having patient contact, and also before leaving a patient's room after having patient contact. As another example, in the foodservice industry it is generally recommended that employees wash their hands after busing, cleaning tables, or touching any unsanitary object.

Despite the importance of frequent hand-washing, compliance with recommended hand-washing practices remains low. There are many possible reasons for this noncompliance. For example, some people simply forget to wash their hands. Others may not realize how infrequently they and their colleagues comply with recommended hand-washing practices. Others still may not fully understand the benefits of hand-washing. Some or all of these issues may be addressed if means were provided to monitor compliance with recommended hand-washing practices.

SUMMARY OF THE INVENTION

A method for monitoring compliance with recommended hand-washing practices is disclosed. The method involves detecting the occurrence of an event that is specified in a hand-washing rule. The method also involves determining whether a person who is involved in the event complies with the hand-washing rule. If the person does not comply with the hand-washing rule, the method may involve triggering a reminder alarm. The alarm may include visual aspects and/or audible aspects. The method may also involve determining whether the person washes his or her hands within a period of time subsequent to the reminder alarm. Compliance data that is related to compliance with the hand-washing rule may be updated.

The hand-washing rule may also include a time period. In this situation, a person may comply with the hand-washing rule if the person washes his or her hands within the specified time period before the occurrence of the event.

The compliance data may include a compliance percentage. Alternatively, or in addition, the compliance data may include a log which includes compliance information about events that have occurred over a period of time. Some or all of the compliance data may be displayed. Additionally, some or all of the compliance data may be transmitted to a computing device, such as a personal digital assistant and/or personal computer, for further analysis.

A hand-washing compliance monitoring unit is also disclosed. The compliance monitoring unit includes an event detector that detects the occurrence of an event that is specified in a hand-washing rule. The compliance monitoring unit also includes a hand-washing detector that detects when a person washes his or her hands. A control unit is also provided. The control unit is in electronic communication with the event detector and with the hand-washing detector. The control unit determines whether the person involved in the event complies with the hand-washing rule. The control unit may be set to trigger a reminder alarm if the person does not comply with the hand-washing rule. The control unit also updates compliance data that is related to compliance with the hand-washing rule.

The hand-washing detector may take the form of a sensor that detects the discharge of a hand-washing agent from a hand-washing agent dispenser. The event may be a person entering or leaving a room in an institution where hand hygiene is important, and the event detector may take the form of a motion detector.

The compliance monitoring unit may also include a speaker. The speaker may be in electronic communication with the control unit. The control unit causes the speaker to play an audible message in response to the occurrence of the event.

The compliance monitoring unit may also include a communication interface in electronic communication with the control unit. The control unit may cause the hand-washing rule to be received from a computing device via the communication interface. The control unit may also cause the compliance data to be transmitted to a computing device via the communication interface.

The compliance monitoring unit may also include a display device in electronic communication with the control unit. The control unit may cause the display device to display the compliance data.

DETAILED DESCRIPTION

It will be readily understood that the components of the embodiments as generally described and illustrated in the Figures herein could be arranged and designed in a wide variety of different configurations. Thus, the following more detailed description of certain exemplary embodiments of the present invention is not intended to limit the scope of the invention, as claimed, but is merely representative of the embodiments of the invention.

The word "exemplary" is used exclusively herein to mean "serving as an example, instance, or illustration." Any embodiment described herein as "exemplary" is not necessarily to be construed as preferred or advantageous over other embodiments.

Reference throughout this specification to "one embodiment" or "an embodiment" means that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment.

Furthermore, the described features, structures, or characteristics may be combined in any suitable manner in one or more embodiments. In the following description, numerous specific details are shown to provide a thorough understanding of embodiments of the invention. One skilled in the relevant art will recognize, however, that the invention may be practiced without one or more of the specific details, or with other methods, components, materials, etc. In other instances, well-known structures, materials, or operations are not shown or described in detail to avoid obscuring aspects of the invention.

Figure 1:
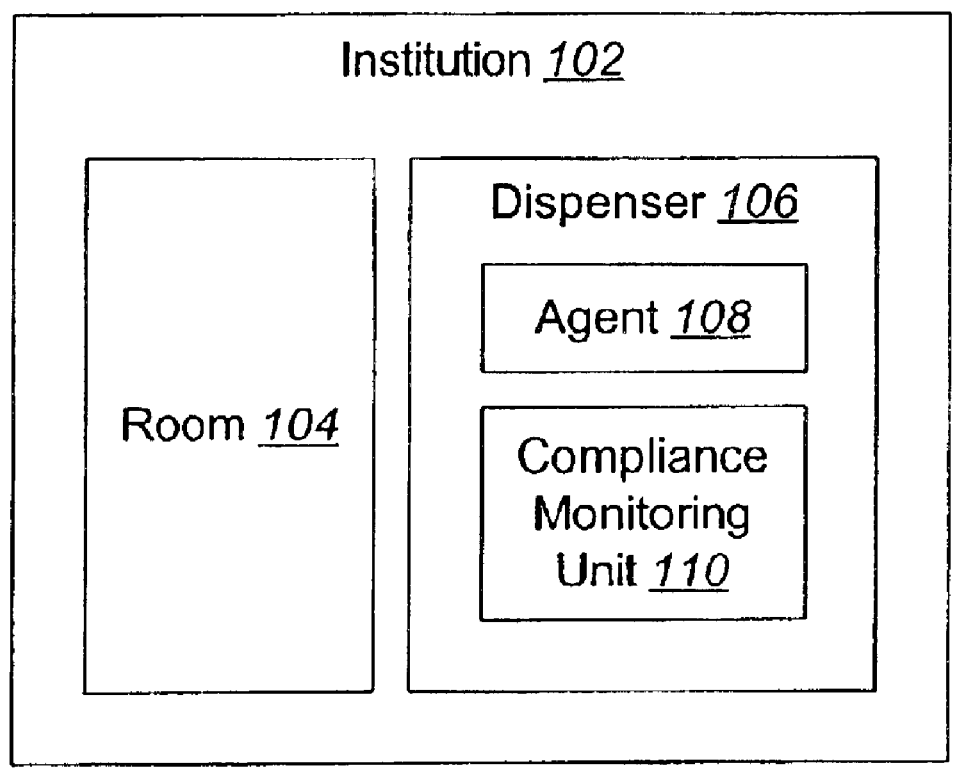
FIG. 1 is a block diagram illustrating an exemplary environment in which some embodiments of the present invention may be practiced.

FIG. 1 is a block diagram illustrating an exemplary environment in which some embodiments of the present invention may be practiced. As shown in FIG. 1, embodiments of the present invention may be used in any institution 102 where hand hygiene is important. Examples of such institutions 102 include hospitals and other healthcare facilities, restaurants, libraries, schools, airports, and the like.

To encourage frequent hand-washing, a hand-washing agent dispenser 106 is typically placed in close proximity to a room 104 within the institution 102. The dispenser 106 may be located either inside or outside the room 104. In one embodiment, the room 104 is a patient room in a hospital.

The hand-washing agent dispenser 106 is any suitable mechanism for dispensing a hand-washing agent 108. When a person washes his or her hands, a hand-washing agent 108 is discharged from the hand-washing agent dispenser 106. One example of a hand-washing agent dispenser 106 is an antimicrobial solution dispenser. Another example of a hand-washing agent dispenser 106 is a soap dispenser that is located in close proximity to a sink.

A hand-washing compliance monitoring unit 110 is also provided. The compliance monitoring unit 110 is capable of determining when the hand-washing agent 108 is discharged from the hand-washing agent dispenser 106. As shown in FIG. 1, the compliance monitoring unit 110 may be a part of the hand-washing agent dispenser 106. Alternatively, the compliance monitoring unit 110 may be separate from the dispenser 106.

The compliance monitoring unit 110 monitors compliance with recommended hand-washing practices. When such compliance does not occur, the compliance monitoring unit 110 may be used to remind individuals to wash their hands. The compliance monitoring unit 110 may also store hand-washing compliance data. Various exemplary embodiments of the compliance monitoring unit 110 will be described below.

Figure 2:
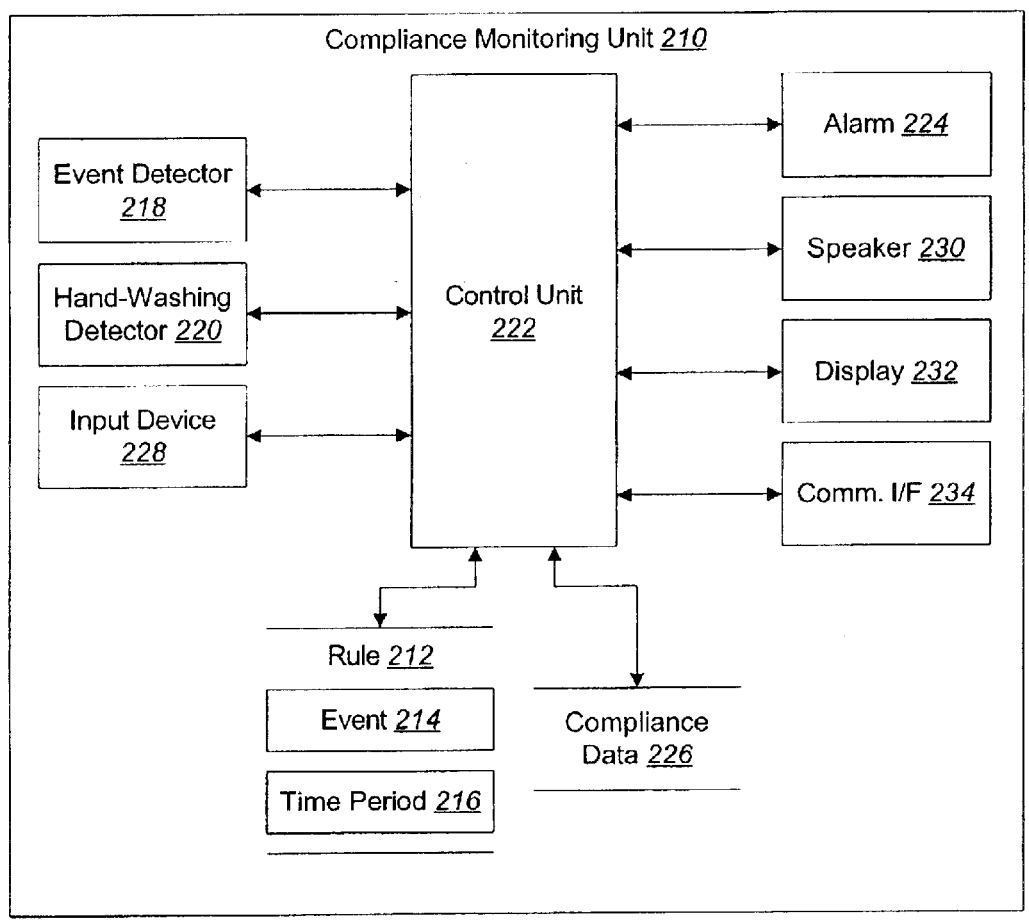
FIG. 2 is a block diagram illustrating logical components in an embodiment of a hand-washing compliance monitoring unit.

FIG. 2 is a block diagram illustrating logical components in an embodiment of a hand-washing compliance monitoring unit 210. Those skilled in the art will appreciate that the logical components in FIG. 2 may be implemented as electronic hardware, mechanical hardware, computer software, or combinations thereof. Whether these logical components are implemented as hardware or software depends upon the particular application and design constraints imposed on the overall system. Skilled artisans may implement these logical components in varying ways for different applications, but such implementation decisions should not be interpreted as causing a departure from the scope of the present invention.

The compliance monitoring unit 210 shown in FIG. 2 includes a hand-washing rule 212. The hand-washing rule 212 specifies a particular hand-washing practice that should be followed. In the embodiment shown in FIG. 2, the hand-washing rule 212 includes an event 214 and a time period 216. In one embodiment, a person complies with the hand-washing rule 212 if he or she washes his or her hands within the specified time period 216 before the occurrence of the event 214. Examples of events 214 that may be specified in the hand-washing rule 212 include entering a room 104 in an institution 102 (such as a patient room in a hospital), leaving a room 104 in an institution 102, and either entering or leaving a room 104 in an institution 102. Although only one hand-washing rule 212 is shown in FIG. 2, alternative embodiments of the compliance monitoring unit 210 may include more than one hand-washing rule 212.

The compliance monitoring unit 210 also includes an event detector 218. The event detector 218 detects the occurrence of the event 214 that is specified in the hand-washing rule 212.

In some embodiments, the event 214 specified in the rule 212 involves a person either entering or leaving a room 104 in an institution 102. In such embodiments, the event detector 218 may be embodied as a motion detector. Those skilled in the art will recognize that the motion detector may detect motion through the use of active and/or passive detecting techniques. In addition to being able to detect motion, the motion detector may also be able to determine the direction of the detected motion. For example, the motion detector may be able to determine whether a person is entering or leaving the room 104.

The compliance monitoring unit 210 also includes a hand-washing detector 220 that detects when a person washes his or her hands. The hand-washing detector 220 may be embodied as a sensor that detects the discharge of a hand-washing agent 108 from a hand-washing agent dispenser 106. For example, the sensor may detect the discharge of antimicrobial solution from an antimicrobial solution dispenser. As another example, the sensor may detect the discharge of soap from a soap dispenser that is located in close proximity to a sink. In some embodiments, more than one hand-washing detector 220 may be provided. The hand-washing detector 220 may be located in, with, or near the compliance monitoring unit 210. Alternatively, the hand-washing detector 220 may be located at a remote location. Communication between the hand-washing detector 220 and the compliance monitoring unit 210 may occur through direct electrical connections or through wireless telemetry.

The compliance monitoring unit 210 also includes a control unit 222. When the event 214 specified in the hand-washing rule 212 occurs, the control unit 222 determines whether the person involved in the event 214 complies with the rule 212. For the rule 212 shown in FIG. 2, this involves determining whether a person has washed his or her hands within the specified time period 216 prior to the event 214. Typically, this involves comparing the time at which a signal is received from the event detector 218 with the time at which a signal is received from the hand-washing detector 220.

After the occurrence of the event 214 in the hand-washing rule 212, the control unit 222 may determine that the rule 212 has not been complied with. In this circumstance, the control unit 222 may trigger a reminder alarm 224. The alarm 224 may include visual aspects and/or audible aspects. The purpose of the alarm 224 is to encourage the person to wash his or her hands.

Following the alarm 224, the control unit 222 may then determine whether the person washes his or her hands within a certain period of time after the alarm 224 is triggered. The period of time may correspond to the time period 216 specified in the hand-washing rule 212. Alternatively, a different time period may be specified in the rule 212 or elsewhere.

The compliance monitoring unit 210 may include hand-washing compliance data 226. The compliance data 226 is related to compliance with the hand-washing rule 212. Various exemplary embodiments of the compliance data 226 will be described below. The hand-washing compliance data 226 is typically updated by the control unit 222 each time the event 214 occurs.

The compliance monitoring unit 210 also includes an input device 228. The input device 228 is capable of being activated by a user of the compliance monitoring unit 210. When a user activates the input device 228, the control unit 222 temporarily suspends performance of one or more of its functions. For example, the control unit 222 may temporarily stop determining compliance with the rule 212, triggering the alarm 224, and/or updating the compliance data 226.

The compliance monitoring unit 210 also includes a speaker 230. In some embodiments, the control unit 222 causes the speaker 230 to play an audible message in response to the occurrence of the event 214 specified in the hand-washing rule 212. The audible message may be a customized message that is recorded by a user of the compliance monitoring unit 210.

The compliance monitoring unit 210 also includes a display device 232. The control unit 222 causes some or all of the hand-washing compliance data 226 to be displayed on the display device 232.

The compliance monitoring unit 210 also includes a communication interface 234. The communication interface 234 facilitates electronic communication between the compliance monitoring unit 210 and a computing device. The communication interface 234 may support wireless (e.g., Bluetooth, infrared, etc.) and/or wired communication. In some embodiments, the hand-washing rule 212 is uploaded from a computing device via the communication interface 234. For example, the rule 212 may be uploaded from a portable computing device, such as a PDA or desktop PC. In this way, rules 212 can be easily added to and/or deleted from the monitoring unit 210, even if the monitoring unit 210 itself is difficult to move. Alternatively, or in addition, the compliance data 226 may be transmitted to a computing device via the communication interface 234. For example, the compliance data 226 may be transmitted to a portable computing device, which may then retransmit the compliance data 226 to a personal computer. In this way, software running on the personal computer may be used to study and analyze the compliance data 226.

Figure 3:
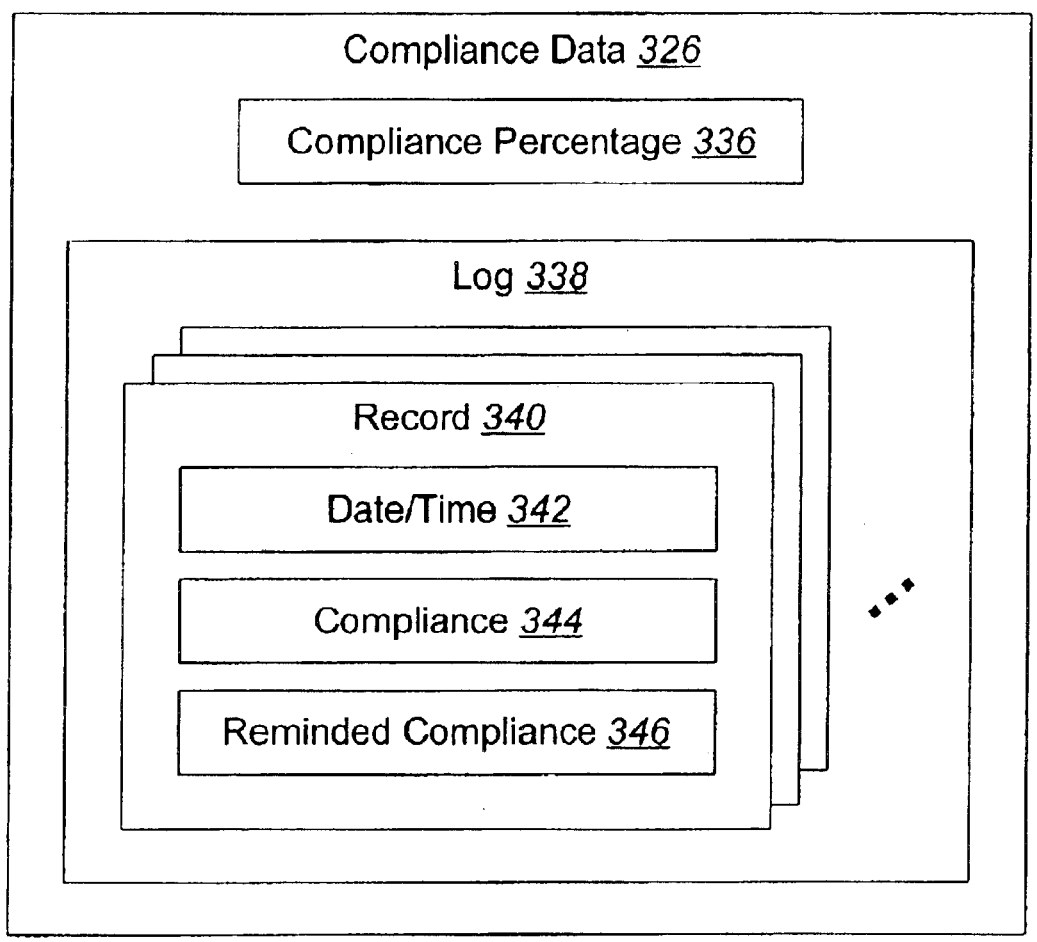
FIG. 3 is a block diagram illustrating an embodiment of the hand-washing compliance data.

FIG. 3 is a block diagram illustrating an embodiment of the hand-washing compliance data 326. As shown, the compliance data 326 may include a compliance percentage 336. The compliance percentage 336 may indicate the percentage of the time that the hand-washing rule 212 is followed. In some embodiments, if a person does not comply with the rule 212 but does wash his or her hands after a reminder alarm 224, this may be counted as a compliance for purposes of calculating the compliance percentage 336.

The compliance data 326 may also include a log 338 which includes compliance information about events 214 that have occurred over a period of time. The log 338 may include a plurality of records 340. A record 340 is created each time the event 214 within the hand-washing rule 212 occurs. Each record 340 includes a date/time field 342, a compliance field 344, and a reminded compliance field 346. The date/time field 342 indicates the date and time that the corresponding event 214 occurred. The compliance field 344 indicates whether the person involved in the event 214 complied with the hand-washing rule 212. If the person did not comply with the hand-washing rule 212, the reminded compliance field 346 indicates whether the person washed his or her hands after a reminder alarm 224.

Figure 4:
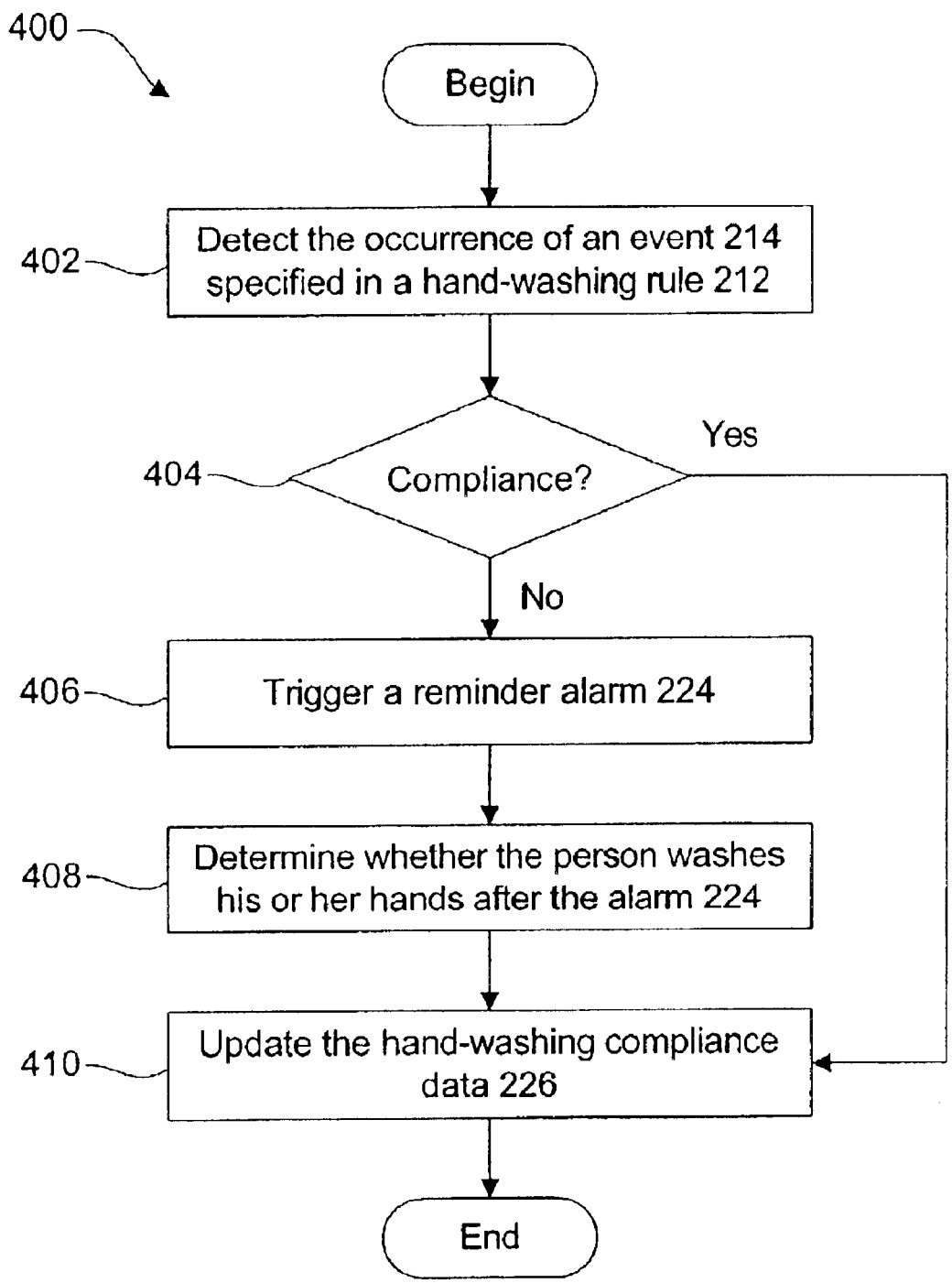
FIG. 4 is a block diagram illustrating an embodiment of a method for monitoring compliance with recommended hand-washing practices.

FIG. 4 is a block diagram illustrating an embodiment of a method 400 for monitoring compliance with recommended hand-washing practices. The method 400 may be implemented by the logical components shown in FIG. 2 and described in connection therewith. The order of the steps or actions shown in FIG. 4 is for illustrative purposes only and is not meant to imply a required order.

The method 400 begins when the compliance monitoring unit 110 detects 402 the occurrence of an event 214 specified in a hand-washing rule 212. As mentioned previously, examples of events 214 that may be specified in the hand-washing rule 212 include a person entering a room 104 in an institution 102 and a person leaving a room 104 in an institution 102.

The method 400 then involves determining 404 whether the person involved in the event 214 detected in step 402 complies with the hand-washing rule 212. This may involve determining 404 whether the person washes his or her hands within a time period 216 specified in the rule 212.

If the hand-washing rule 212 has not been complied with, a reminder alarm 224 is then triggered 406. The method 400 then involves determining 408 whether the person involved in the event 214 washes his or her hands within a certain period of time subsequent to the reminder alarm 224.

The method 400 then involves updating 410 the hand-washing compliance data 226. This may involve recalculating the compliance percentage 436 and/or creating a new record 340 in a log 338. If in step 404 it is determined that the hand-washing rule 212 has been complied with, the method 400 may proceed directly to step 410.

Figure 5A:
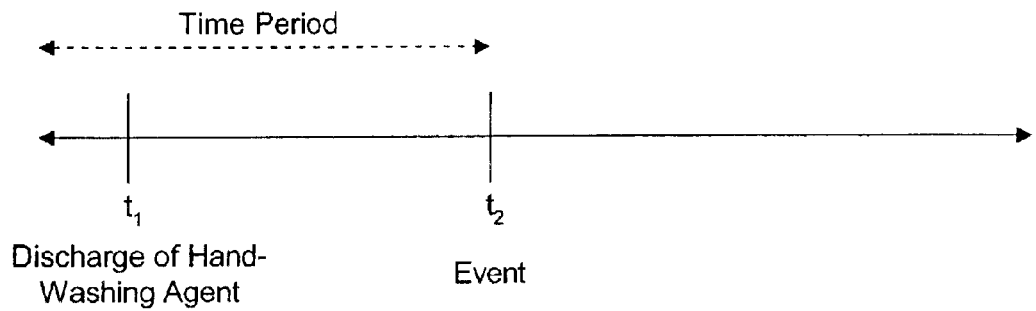
FIG. 5A is a timing diagram illustrating the behavior of a person who complies with an exemplary hand-washing rule.

FIG. 5A is a timing diagram illustrating the behavior of a person who complies with an exemplary hand-washing rule 212. The vertical lines in the timing diagram represent successive moments in time, i.e., time $t_2$ occurs after time $t_1$. As mentioned previously, a hand-washing rule 212 may include an event 214 and a time period 216. A person complies with the hand-washing rule 212 if he or she washes his or her hands within the specified time period 216 before the occurrence of the event 214.

The hand-washing detector 220 detects the discharge of hand-washing agent 108 from a hand-washing agent dispenser 106 at time $t_1$. The event detector 218 detects the occurrence of an event 214 at time $t_2$. For example, the event detector 218 may be a motion detector that detects motion in the doorway to a room 104 in an institution 102. As shown, the person involved in the event 214 washed his or her hands within the time period 216 specified in the hand-washing rule 212 before the occurrence of the event 214. Thus, the person involved in the event 214 has complied with the hand-washing rule 212.

Figure 5B:
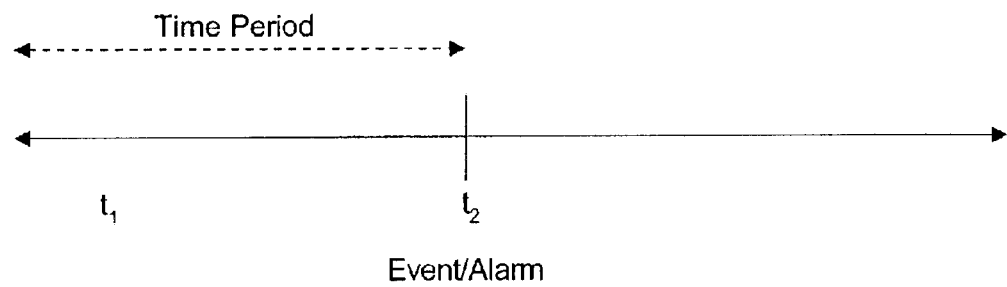
FIG. 5B is a timing diagram illustrating the behavior of a person who does not comply with an exemplary hand-washing rule.

FIG. 5B is a timing diagram illustrating the behavior of a person who does not comply with an exemplary hand-washing rule 212. As shown, the event detector 218 detects the occurrence of an event 214 at time $t_2$. However, the hand-washing detector 220 did not detect the discharge of hand-washing agent 108 from the hand-washing agent dispenser 106 within the time period 216 before the occurrence of the event 214. Thus, the person involved in the event 214 has not complied with the hand-washing rule 212. As described above, an alarm 224 may be triggered to remind the person to wash his or her hands.

Figure 5C:
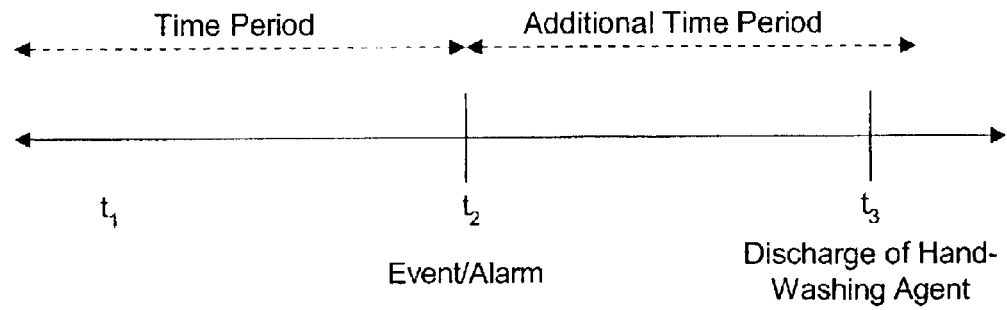
FIG. 5C is a timing diagram illustrating the behavior of a person who does not comply with an exemplary hand-washing rule but who does wash his or her hands after an alarm is triggered.

FIG. 5C is a timing diagram illustrating the behavior of a person who does not comply with an exemplary hand-washing rule 212 but who does wash his or her hands after an alarm 224 is triggered. As in FIG. 5B, the hand-washing detector 220 does not detect the discharge of hand-washing agent 108 from the hand-washing agent dispenser 106 within the time period 216 before the occurrence of the event 214 at time $t_2$. Thus, the person involved in the event 214 has not complied with the hand-washing rule 212. Therefore, an alarm is triggered at time $t_2$. The person then washes his or her hands at time $t_3$, which falls within an additional time period that is measured subsequent to the triggering of the alarm 224.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A method for monitoring compliance with recommended hand-washing practices in an institution where hand hygiene is important, comprising:

detecting the occurrence of an event specified in a hand-washing rule associated with a room in the institution, wherein the event involves a person;

determining whether the person complies with the hand-washing rule;

triggering a reminder alarm if the person does not comply with the hand-washing rule; and updating compliance data associated with the room that is related to compliance with the hand-washing rule, wherein the compliance data associated with the room comprises a compliance percentage.

2. The method as defined in claim 1, wherein the event is selected from the group consisting of the person entering the room in the institution and the person leaving the room in the institution.

3. The method as defined in claim 1, wherein the hand-washing rule also specifies a time period, and wherein the person complies with the hand-washing rule if the person washes his or her hands within the specified time period before the occurrence of the event.

4. The method as defined in claim 1, further comprising determining whether the person washes his or her hands within a period of time subsequent to the reminder alarm.

5. The method as defined in claim 1, further comprising playing an audible message in response to the occurrence of the event.

6. The method as defined in claim 1, further comprising receiving the hand-washing rule from a computing device.

7. The method as defined in claim 1, further comprising transmitting the compliance data associated with the room to a computing device.

8. The method as defined in claim 1, further comprising displaying the compliance data associated with the room.

9. The method as defined in claim 1, wherein the compliance data associated with the room comprises a log which includes compliance information about events that have occurred in the room over a period of time.

10. A hand-washing compliance monitoring unit for use in an institution where hand hygiene is important, comprising:

an event detector that detects the occurrence of an event that is specified in a hand-washing rule, wherein the event involves a person, wherein the event detector is associated with a room in the institution;

a hand-washing detector that detects when the person washes his or her hands; and a control unit in electronic communication with the event detector and with the hand-washing detector, wherein the control unit determines whether the person complies with the hand-washing rule, associated with the room, triggers a reminder alarm if the person does not comply with the hand-washing rule, and updates compliance data associated with the room that is related to compliance with the hand-washing rule, wherein the compliance data associated with the room comprises a compliance percentage.

11. The compliance monitoring unit as defined in claim 10, wherein the event is selected from the group consisting of the person entering the room in the institution and the person leaving the room in the institution, and wherein the event detector comprises a motion detector.

12. The compliance monitoring unit as defined in claim 10, wherein the hand-washing detector comprises a sensor that detects the discharge of a hand-washing agent from a hand-washing agent dispenser in close proximity to the room.

13. The compliance monitoring unit as defined in claim 12, wherein the hand-washing agent dispenser comprises an antimicrobial solution dispenser.

14. The compliance monitoring unit as defined in claim 12, wherein the hand-washing agent dispenser comprises a soap dispenser in close proximity to a sink.

15. The compliance monitoring unit as defined in claim 10, wherein the hand-washing rule also specifies a time period, and wherein the person complies with the hand-washing rule if the person washes his or her hands within the specified time period before the occurrence of the event.

16. The compliance monitoring unit as defined in claim 10, further comprising a speaker in electronic communication with the control unit, wherein the control unit causes the speaker to play an audible message in response to the occurrence of the event.

17. The compliance monitoring unit as defined in claim 10, further comprising a communication interface in electronic communication with the control unit, wherein the control unit causes the hand-washing rule to be received from a computing device via the communication interface.

18. The compliance monitoring unit as defined in claim 10, further comprising a communication interface in electronic communication with the control unit, wherein the control unit causes the compliance data associated with the room to be transmitted to a computing device via the communication interface.

19. The compliance monitoring unit as defined in claim 10, further comprising a display device in electronic communication with the control unit, wherein the control unit causes the display device to display the compliance data associated with the room.

20. A hand-washing compliance monitoring unit associated with a room in an institution where hand hygiene is important, comprising:
  means for detecting the occurrence of an event specified in a hand-washing rule, wherein the event involves a person, wherein the means for detecting is associated with the room in the institution;
  means for determining whether the person complies with the hand-washing rule;
  means for triggering a reminder alarm if the person does not comply with the hand-washing rule; and
  means for updating compliance data associated with the room that is related to compliance with the hand-washing rule, wherein the compliance data associated with the room comprises a compliance percentage.

21. The compliance monitoring unit as defined in claim 20, wherein the hand-washing rule also specifies a time period, and wherein the person complies with the hand-washing rule if the person washes his or her hands within the specified time period before the occurrence of the event.

22. The compliance monitoring unit as defined in claim 20, further comprising means for determining whether the person washes his or her hands within a period of time subsequent to the reminder alarm.

23. The method as defined in claim 7, wherein the computing device operates software which studies and analyzes the compliance data.

* * * * *